(12) United States Patent
Huo et al.

(10) Patent No.: US 10,598,630 B2
(45) Date of Patent: Mar. 24, 2020

(54) CHARACTERIZATION AND FAILURE ANALYSIS OF A SENSOR USING IMPEDANCE FREQUENCY RESPONSE SPECTRA

(71) Applicant: Endress+Hauser Conducta Inc., Anaheim, CA (US)

(72) Inventors: Jinshan Huo, Corona, CA (US); Michael Hanko, Dresden (DE)

(73) Assignee: Endress+Hauser Conducta Inc., Anaheim, CA (US)

( * ) Notice: Subject to any disclaimer, the term of this patent is extended or adjusted under 35 U.S.C. 154(b) by 163 days.

(21) Appl. No.: 15/283,022

(22) Filed: Sep. 30, 2016

(65) Prior Publication Data

US 2018/0095054 A1  Apr. 5, 2018

(51) Int. Cl.
*G01N 27/416* (2006.01)
*G01N 27/02* (2006.01)

(52) U.S. Cl.
CPC ....... *G01N 27/4165* (2013.01); *G01N 27/026* (2013.01)

(58) Field of Classification Search
CPC .............. G01N 27/4165; G01N 27/026
See application file for complete search history.

(56) References Cited

U.S. PATENT DOCUMENTS 5,489,849 A * 2/1996 Sadoway ............... G01N 27/02
204/406
2002/0027085 A1  3/2002 Stori
2014/0095102 A1 * 4/2014 Potyrailo ............... G01R 27/28
702/127
2014/0278013 A1 * 9/2014 Gibson ................... G01R 27/02
701/108
2015/0059484 A1 * 3/2015 Dawson ............... G01L 9/0072
73/718
2015/0164371 A1 * 6/2015 Varsavsky ............ A61B 5/0537
600/347
2017/0205314 A1 * 7/2017 McQuillen .......... G01M 15/104

FOREIGN PATENT DOCUMENTS

WO   2007/006695 A1   1/2007

\* cited by examiner

*Primary Examiner* — Christopher P McAndrew
*Assistant Examiner* — Zannatul Ferdous
(74) *Attorney, Agent, or Firm* — Christopher R. Powers; PatServe

(57) ABSTRACT

According to at least one aspect of the present disclosure, a method includes applying an alternating current having a frequency at a selected voltage to a sensor, wherein the voltage is applied between a reference electrode and a working electrode of the sensor, varying the frequency of the alternating current between a lower frequency and an upper frequency, measuring an impedance of the sensor between the reference electrode and the working electrode as a function of the frequency of the alternating current, analyzing the measured impedance to determine a total impedance of the sensor and the real and imaginary components of the total impedance at each applied frequency of the alternating current, and characterizing the sensor based on the total impedance at the low frequency end of the sensor and on the real and imaginary components of the total impedances.

22 Claims, 12 Drawing Sheets

CHARACTERIZATION AND FAILURE ANALYSIS OF A SENSOR USING IMPEDANCE FREQUENCY RESPONSE SPECTRA

TECHNICAL FIELD

The present disclosure generally relates to characterizing measuring sensors, particularly characterizing electrochemical measuring sensors.

BACKGROUND

Measuring sensors, particularly electrochemical measuring sensors, are widely used for quality monitoring, process control and research in agriculture, beverages, foods, water, various industries and research labs. Such measuring sensors include pH sensors. A critical component of a pH sensor is a pH glass membrane. Generally, pH glass material used in the pH glass membrane is specially formulated to make the material sensitive to hydrogen ions ($H^+$).

Conventionally, to test and verify the proper functioning of a pH sensor, the sensor is placed in contact with a standard buffer solution of known pH (e.g., pH 4, 7 and 10 buffers), and the sensor's signal output is displayed and verified using a pH meter. Certain pH meters include a function to measure glass impedance. However, such meters are not accurate enough or capable to distinguish sensor failure modes, such as a crack in the glass membrane or a short circuit in the sensor.

If in case a sensor failed to work normally, for whatever reason (e.g., harsh application conditions, inappropriate selection of sensor type, manufacturing processes, changes of material/part supply etc.), physical examination and often destruction (e.g., dissection) of the sensor has previously been the only way to determine the failure mode and root cause of failure of the sensor. However, dissecting a pH sensor can be very time consuming. In addition, it is not guaranteed to see root cause after dissection. For example, a micro-crack at the pH glass membrane/glass stem interface in transversal direction may not be visible. More often, dissection can easily damage the signs of root cause because of the complex construction of a pH sensor, which is usually built with materials of wide range mechanical and physical properties—from liquid and soft rubber, to hard plastic, rigid epoxy, and very hard but brittle glass.

Accordingly, there remains a need for further contributions in this area of technology to enable a method to characterize failure modes and to determine the root cause of such failures a measuring sensor.

BRIEF SUMMARY

According to at least one aspect of the present disclosure, a method for characterization and failure analysis of a measuring sensor is disclosed. The method includes applying an alternating current having a frequency at a selected voltage to a sensor, where the voltage is applied between a reference electrode and a working electrode of the sensor. The frequency of the alternating current is varied between a lower frequency and an upper frequency over a range from a lower frequency end to an upper frequency end. The method includes measuring an impedance of the sensor between the reference electrode and the working electrode over the range of frequencies of the alternating current. The measured impedance is analyzed to determine one or more total impedance of the sensor and the real and imaginary components of the one or more total impedance at and over the applied frequencies of the alternating current. The sensor is characterized based on the one or more total impedance and on the real and imaginary components of the one or more total impedance. The method can further include generating a measured impedance frequency response spectrum.

In an embodiment, the characterizing includes identifying whether the total impedance at low frequency end is below a lower threshold or above an upper threshold and/or whether imaginary components at various frequencies are predominantly greater than or less than zero.

In an embodiment, the method characterizes a sensor in which the total impedance at low frequency end is below the lower threshold and the imaginary components at various frequencies are predominantly greater than zero as having a defect in a membrane of the sensor. The method may characterizes a sensor in which the total impedance at low frequency end is below the lower threshold and the imaginary components at various frequencies are predominantly less than zero as having a short circuit.

In an embodiment, the lower threshold is around 5 megaohms, and the upper impedance threshold is about 50 megaohms. In an alternate embodiment, the lower threshold is around 10 megaohms, and the upper threshold is about 5 gigaohms.

The method may characterize a sensor in which the total impedance at low frequency end is above the upper threshold and the real/imaginary component ratio at various frequencies is predominantly less than a threshold is characterized as having an open circuit. In an embodiment, the upper threshold is about 5 gigaohms and the ratio threshold is around 0.1.

In an alternate embodiment, the method further includes data fitting the measured impedance to generate a simulated response spectrum and applying an equivalent circuit model to the simulated response spectrum to estimate the capacitance, resistance and Warburg coefficient of the sensor. The characterization of the sensor may include predicting a performance of the sensor using the estimated the capacitance, resistance and Warburg coefficient. The analyzing may include generating a plot of the measured impedance as a function of the frequency of the alternating current to yield a frequency response spectrum. The plot may be a Nyquist plot.

In an embodiment the frequency of the alternating current is varied over a spectrum. Or alternately the frequency of the alternating current is varied between discrete predetermined frequencies.

In an embodiment, the sensor is a pH sensor. The reference electrode may be an external reference electrode connected to or associated with the sensor The sensor may be characterized as a step in a quality control process. The characterization may include determining a failure mode of the sensor. The characterization may include checking a status of the sensor.

In an embodiment, the sensor includes equipment suitable to perform the measuring of the impedance of the sensor. The equipment may be integrated into a plug head of the sensor.

BRIEF DESCRIPTION OF THE DRAWINGS

The described embodiments and other features, advantages and disclosures contained herein, and the manner of attaining them, will become apparent and the present disclosure will be better understood by reference to the following description of various embodiments of the present disclosure taken in junction with the accompanying drawings, wherein.

DETAILED DESCRIPTION

Figure 1:
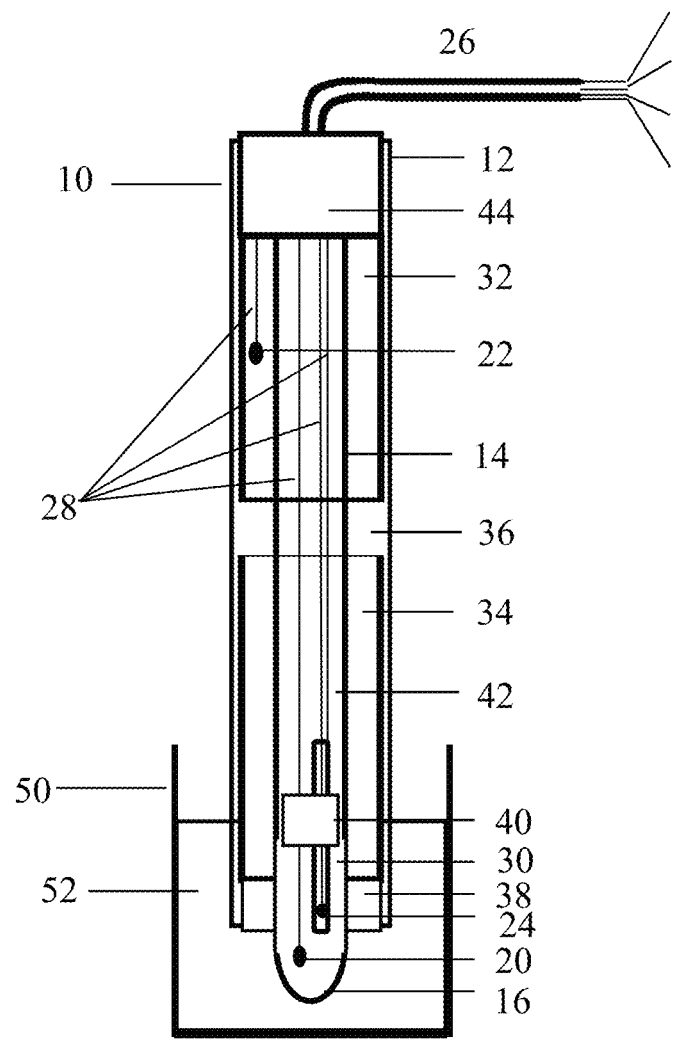
FIG. 1 shows a cross-sectional view of a sensor, according to an embodiment of the present disclosure.

The present application discloses various embodiments of methods for characterization and failure analysis of a measuring sensor. According to one aspect of the present disclosure, methods of applying measured impedance frequency response spectra to sensor characterization are disclosed. According to a further aspect of the present disclosure, methods of applying measured impedance frequency response spectra to sensor failure mode analysis are disclosed, specifically with respect to pH sensors. In certain aspects, the disclosed methods may generally apply a form of electrochemical impedance spectroscopy (EIS). For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended. In particular, the disclosed methods may be applied to measuring sensors other than pH sensors, specifically to electrochemical measuring sensors.

FIG. 1 illustrates a sensor 10 placed in a reservoir 50 containing a test solution 52. The sensor 10 may be an electrochemical measuring sensor including a reference cell containing an internal electrolyte. In certain embodiments, the sensor 10 is a pH sensor. The sensor 10 may include a sensor body 12 within which a tube 14 is disposed. The tube 14 may be a glass tube. As shown in FIG. 1, the tube 14 may include a membrane 16 affixed to a distal end of the tube 14 and a front seal 40, thereby defining a volume containing a first electrolyte 30. The membrane 16 may be a glass membrane made of doped glass formulated to be sensitive to a specific ion. In embodiments in which the sensor 10 is a pH sensor, the membrane 16 is sensitive to hydrogen ions (i.e., $H^+$). A working electrode 20 may be disposed within the first electrolyte 30 such that the working electrode 20 is in electrochemical communication with the test solution 52 through the membrane 16. In embodiments where the sensor 10 is a pH sensor, the working electrode 20 may be referred to as a pH electrode. In certain embodiments, the working electrode 20 may be a silver chloride electrode (i.e., a Ag/AgCl electrode); nonetheless, other types of electrodes are applicable.

The sensor 10 may further include a reference electrode 22 positioned within a volume defined by the sensor body 12, a back seal 44, which seals the proximal ends of both the sensor body 12 and the tube 14, and a middle junction 36, which seals the gap between the sensor boy 12 and the tube 14, such that the defined volume contains a second electrolyte 32. In certain embodiments, the reference electrode 22 may be a silver chloride electrode (i.e., a Ag/AgCl electrode). In certain embodiments, the sensor 10 may include a front junction 38 disposed at the distal end of the sensor body 12 such that the front junction 38 seals the gap between the sensor body 12 and the tube 14 and therewith defines a volume containing a third electrolyte 34. In certain embodiments, as shown in FIG. 1, the sensor 10 may include a temperature sensor 24 disposed adjacent the working electrode 20 and in the first electrolyte 30 to indicate the temperature of the first electrolyte 30. The working electrode 20, reference electrode 22 and the temperature sensor 24 may include lead lines 28 that pass through the back seal 44, are bundled together in a cable 26, and enable electrical communication between these components of the sensor 10 and external sources and meters (not shown). While FIG. 1 illustrates a double junction pH sensor, the disclosed methods may be applied to single junction pH sensors as well as other types of electrochemical measuring sensors.

Where the sensor 10 is a pH sensor, when sensor 10 is placed in contact with the test solution 52, the charge distributions at the interfaces of the membrane 16 to test solution 52 and of the membrane 16 to first electrolyte 30 are strongly affected by the H+ ions in the test solution 52. At equilibrium, the potential at membrane/test solution interface, $E_{g/s}$, is a function of $H^+$ activity, $a_{H^+}$:

$$E_{g/s} \sim 2.3026 \frac{RT}{F} \log(a_{H^+}) \qquad \text{[EQN. 1]}$$

where R is the molar gas constant 8.3144 J mol$^{-1}$ K$^{-1}$, T is the temperature in Kelvin, F is the Faraday constant 96,485.3 C·mol$^{-1}$, and 2.3026 is a conversion between natural and common logarithm. Since the pH of the first electrolyte 30 within the membrane 16, the potential of working electrode 20, and the potential of the reference electrode 22 are all constants, the overall potential difference between pH and Ref electrodes is:

$$\Delta E_{pH\text{-}Ref} = E' + 2.3026 \frac{RT}{F} \log(a_{H^+}) \qquad \text{[EQN. 2]}$$

where E' is constant. Since pH is defined as pH=−log($a_{H^+}$), at given temperature, there is linear relationship between $\Delta E_{pH\text{-}Ref}$ and pH:

$$\Delta E_{pH\text{-}Ref} = E' - 1.98 \times 10^{-4} T\text{-}pH \quad [\text{EQN. 3}]$$

For example, $\Delta F_{pH\text{-}Ref}$ is 177.5 mV at pH 4, 0 mV at pH 7, and −177.5 mV at pH 10 at 25° C.; with slope −59.1667. A properly functioning sensor 10 should follow EQN. 3, such that its voltage reading $\Delta E_{pH\text{-}Ref}$ in pH buffer 7 should be 0 mV and the slope should be about −59.17 at 25° C. Usually a small error (e.g., ±12 mV) is acceptable and defined in the specification of the sensor 10.

Given the complexity of the assembly, the sensor 10 may be manufactured with defects that harm the performance of the sensor 10 in operation. For example, poor manufacturing processes, planned and unplanned changes of material or part supply, bad in-coming material or handling, etc. Alternatively, defects may develop during operation due to various factors, such as harsh application conditions, inappropriate selection of sensor, end of life span, wear, etc. One aspect of the present disclosure includes a method to characterize and analyze a sensor to facilitate root cause failure analysis of a sensor without further damaging the sensor under test. In at least one embodiment of the present disclosure, a method of applying measured impedance frequency response spectra to characterize and analyze electrochemical measuring sensors is disclosed. The method will be disclosed with respect to the characterization and analysis of a pH sensor. Nonetheless, the method may be applied of other types of electrochemical sensors, such as electrochemical measuring sensors.

Figure 2:
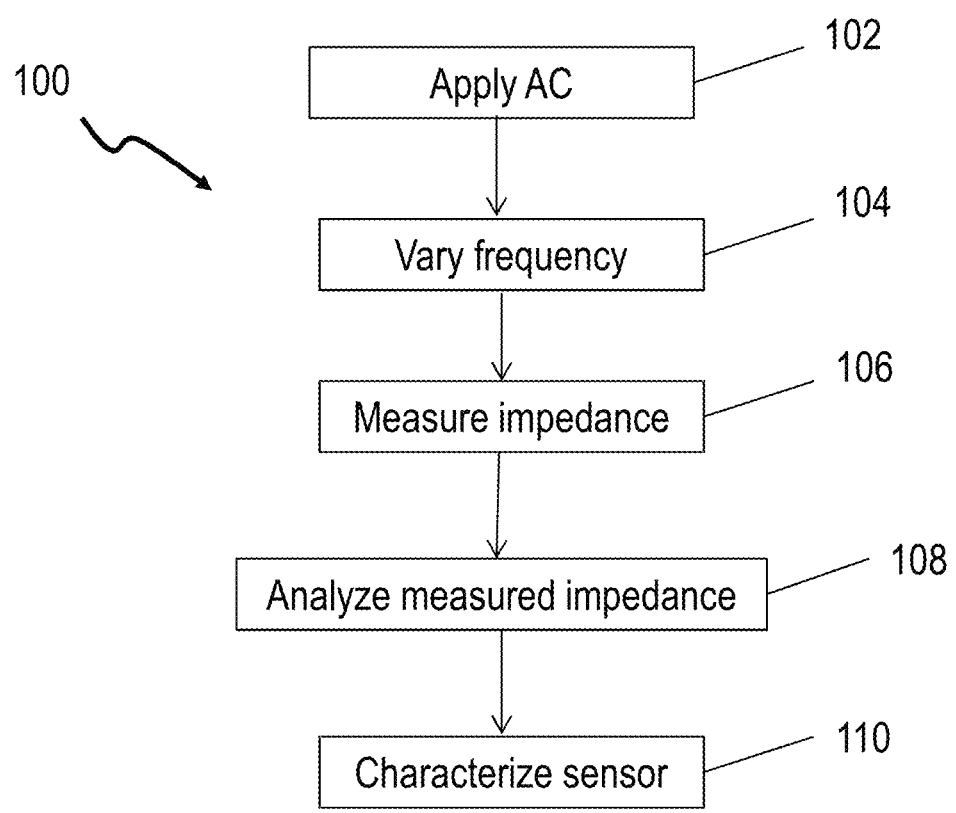
FIG. 2 illustrates a method of characterizing a sensor, according to an embodiment of the present disclosure.

In at least one embodiment of the present disclosure as shown in FIG. 2, a method 100 of characterization and failure analysis of the sensor 10 includes a step 102 of applying an alternating current (AC) at a selected voltage to the sensor 10 between the reference electrode 22 and the working electrode 20. For example, the selected voltage may be relatively small to prevent damaging the sensor 10 but large enough to generate a response from the sensor 10. In at least one embodiment, the selected voltage is around 100 millivolts (mV). The method 100 includes a step 104 of varying the frequency of the AC between a lower frequency and an upper frequency over a range having a low frequency end and an upper frequency end.

In the step 104, the frequency of the applied AC may be varied over a wide range having a low frequency end and an upper frequency end. As used herein, "end" may include a discrete frequency in the range; additionally and alternatively, "end" may include a number of frequencies toward an end region of the range. For example, the range may extend from 1 megahertz (MHz) to 0.01 Hz. In certain embodiments, the frequency of the applied AC may be varied through a scan over a narrower range, such as 300 kHz to 0.01 Hz. In further embodiments, the frequency of the applied AC may be varied in discrete steps between discrete predetermined frequencies from one desired frequency to the next. In such an embodiment, for example, discrete frequencies of 300 kHz, 100 kHz, 50 kHz, 10 kHz, 1 kHz, 1 Hz and 0.01 Hz may be applied to the sensor 10. Accordingly, the varying of the frequency of the AC may include scanning through the desired range of frequencies and selecting discrete frequencies in the range. The AC may be applied by any suitable controlled power source. In at least one embodiment, a potentiostat/galvanostat may be employed to apply the desired frequencies and the selected voltage.

The method 100 further includes a step 106 of measuring an impedance of the sensor 10 between the reference electrode 22 and the working electrode 20 over the range of frequencies of the alternating current. The step 106 may include measuring the impedance frequency response of the sensor 10 or the electrochemical impedance spectrum (EIS) of the sensor 10. The impedance may be measured by any suitable instrument, for example, a potentiostat/galvanostat. In at least one embodiment of the present disclosure, equipment suitable to perform the measuring of the impedance of the sensor may be included in the sensor. Further, the sensor may include equipment suitable to perform all or part of the method 100. For example, the sensor may include hardware, software and firmware suitable to perform all or part of the method 100. In such an embodiment, the equipment may be integrated into a plug head of the sensor. In certain embodiments, the equipment may at least partial include the functionality of a potentiostat/galvanostat.

The method 100 may include a step 108 of analyzing the measured impedance to determine one or more total impedance of the sensor 10 and the real and imaginary components of the one or more total impedance at and over the applied frequencies of the AC. In the step 108, the analysis may include generating a measured impedance frequency response spectrum. The analysis may further include plotting the real part of the total impedance against the imaginary part of the total impedance for the various frequencies to generate a Nyquist plot. The analysis may further include determining a real/imaginary component ratio at various frequencies based the real and imaginary components of the total impedance at a given frequency.

The method 100 may further include a step 110 of characterizing the sensor 10 based on the one or more total impedance of the sensor 10 and on the real and imaginary components of the total impedance. In the step 110, the characterization may be qualitative and/or quantitative as discussed further herein. In certain embodiments, the step 110 includes identifying the failure mode of an improperly operating sensor based on the total impedance of the sensor 10 and on the real and imaginary components of the total impedance. The step 110 may further include determining the root cause of such failure modes. In an alternative application, the method 100 may be used as a quality control measure to qualify newly manufactured sensors before they are employed in the field. 20. In a further embodiment, the characterizing of the sensor includes checking a status of the sensor.

The method 100 has been applied to both functioning and malfunctioning pH sensors in a series of experiments that demonstrate the effectiveness of the method 100. The experiments were conducted on pH sensors manufactured by the Applicant and on pH sensors manufactured by other manufacturers, as noted, using a PMC CHS08A Potentiostat/Galvanostat and 3M KCl solution in a Gamry VistaShield Faraday cage. An AC signal of 100 mV was applied between the working and reference electrodes with a frequency scan from 300 kHz to 0.01 Hz, unless noted otherwise. In certain cases as discussed, the AC signal was applied between the sensor reference electrode and an external reference electrode. pH testing was conducted using Applicant's CM42 pH meter and 200 mL each of pH buffer solutions of 4, 7 and 10 pH.

Figure 3:
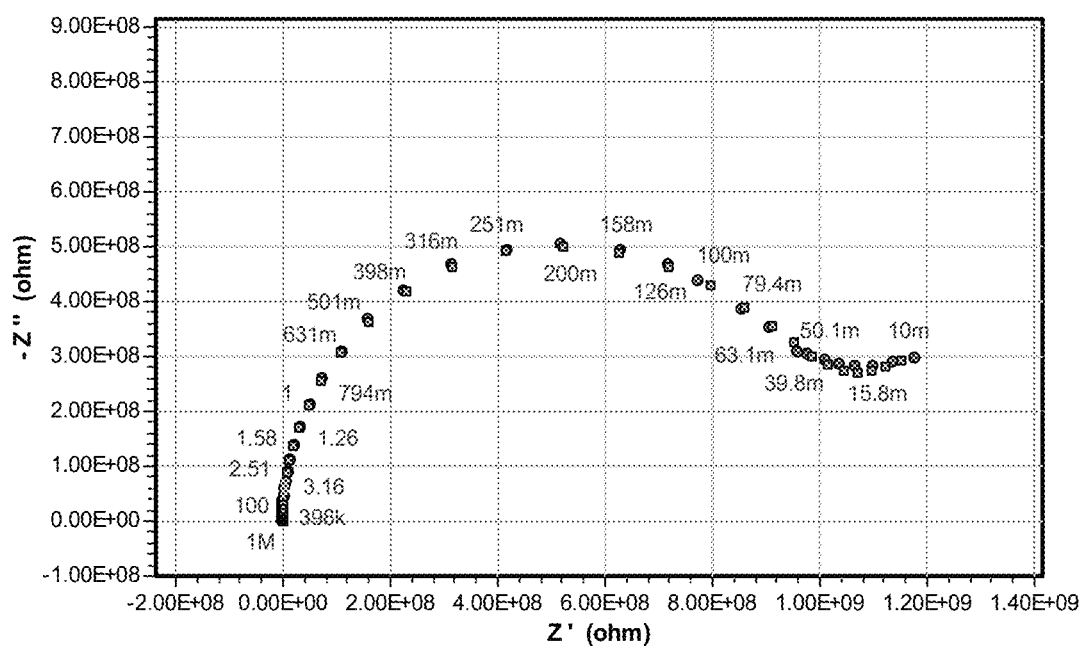
FIG. 3 shows a Nyquist plot of an impedance frequency response spectrum of a properly functioning sensor, according to an embodiment of the present disclosure.

FIG. 3 shows the measured impedance frequency response spectrum of a properly functioning Test Sensor 1. In FIG. 3, the impedance response has been presented in a Nyquist plot with the real part of the total impedance plotted on the x-axis and the imaginary part of the total impedance plotted on the y-axis. Qualitatively, the Nyquist plot exhibits a semicircular portion with a tail at the low frequency end of the response spectrum. Quantitatively, both the real and imaginary parts of the total impedance are positive (i.e., greater than zero) and are in the expected range for the Test Sensor 1. Further, the total impedance at the low frequency end, around 1000 megaohms (Me), is also in the expected range for the test sensor.

Figure 4A:
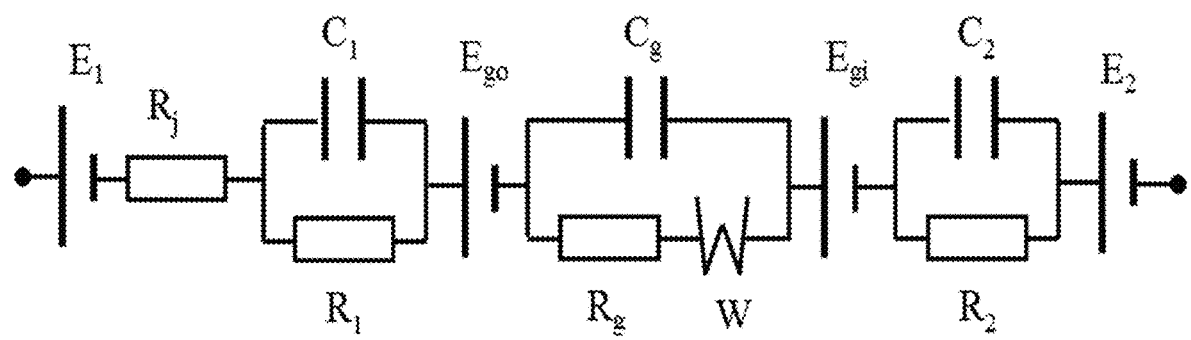
FIGS. 4A and 4B show equivalent circuits, according to exemplary embodiments of the present disclosure.

The electrical behavior of a pH sensor, such as the sensor 10 as shown in FIG. 1, can be characterized with an equivalent circuit, as shown in FIG. 4A. In FIG. 4A, $E_1$ and $E_2$ are the potentials of the reference electrode 22 and the working (i.e., pH) electrode 20, respectively, which are constants and depend on the electrode materials and the first electrolyte 30 and second electrolyte 32 that surround their respective electrodes (i.e., the working electrode 20 and the reference electrode 22). $R_j$ is the total resistance of front and middle junctions 38, 36, the first, second and third electrolytes 30, 32, 34, and the leads 28. $C_1$ and $C_2$ are the double layer capacitances of the reference electrode 22 and the working electrode 20, respectively. $R_1$ and $R_2$ are the electrode/electrolyte resistances of the reference electrode 22 and the working electrode 20, respectively. $C_g$ and $R_g$ are the capacitance and charge transfer resistance across the membrane 16. $E_{go}$ and $E_{gi}$ are the potentials of the outside and inside surfaces of the membrane 16. W is the Warburg coefficient or diffusion element, which includes the diffusion resistance of the membrane 16 and has units of $\Omega \cdot s^{-1/2}$. The Warburg coefficient may also be represented by "σ".

The impedance of the Warburg diffusion element can be expressed as:

$$Z_w = \sigma/\omega^{1/2} j\sigma/\omega^{1/2} \qquad [\text{EQN. 4}]$$

where $\omega=2\pi f$, f is frequency, σ is Warburg coefficient ($ohm \cdot s^{-1/2}$). The Warburg coefficient can be calculated from the admittance, $Y_o$, which may be obtained from data fitting by simulation software:

$$\sigma = \frac{\sqrt{2}}{2Y_o} \qquad [\text{EQN. 5}]$$

Figure 4B:
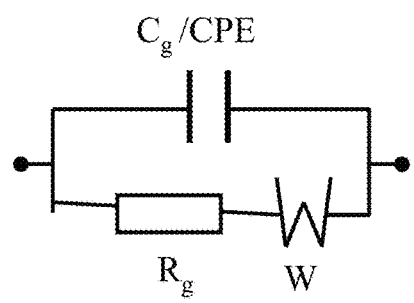

Among the components in FIG. 1, the impedance of membrane 16 (i.e., $C_g/(R_g W)$) of a conventional pH sensor is typically in a range of hundreds of megaohms (MΩ) and can be as high as a few gigaohms (GΩ). In comparison, the impedances of the other components are very small. Hence, the equivalent circuit can be simplified as shown in FIG. 4B. Referring to FIG. 3, the circular data points plot the measured impedance data. The square data points are fitting points obtained using data fitting/simulation software, ZSimpWin, to fit the equivalent circuit model of FIG. 4B to the measured impedance. For the data presented in FIG. 3, the data fit calculated an equivalent $C_g = 7.2 \times 10^{-4}$ μF, $R_g = 946$ MΩ and $W = 5.89 \times 10^7$ $\Omega \cdot s^{-1/2}$. These values are in line with expected capacitance, resistance and diffusion resistance of a properly functioning pH sensor.

A Nyquist plot of certain sensors may exhibit a semicircular portion that appears to be slightly compressed in vertical axis, yet with the characteristic tail at the low frequency end of the response spectrum. Such a slightly compressed appearance indicates that the simulation component, $C_g$, is not an ideal capacitor. With such a sensor, the equivalent circuit of FIG. 4B should include a constant phase element (CPE) instead of $C_g$ for generate a more accurate data fit. The corresponding capacitance value then can be calculated from the following equations:

$$\frac{1}{Z} = Y = Q_o(j)^n \qquad [\text{EQN. 6}]$$

$$C = Q_o(\omega_{max})^{n-1} \qquad [\text{EQN. 7}]$$

where Z is CPE impedance, Y is Admittance, $Q_o$ and n can be obtained from data fitting by simulation software, 0<n<1; for pure capacitor, n=1. Accordingly, the simulation software can vary the n parameter to best fit the data and calculate the corresponding capacitance value.

Figure 5:
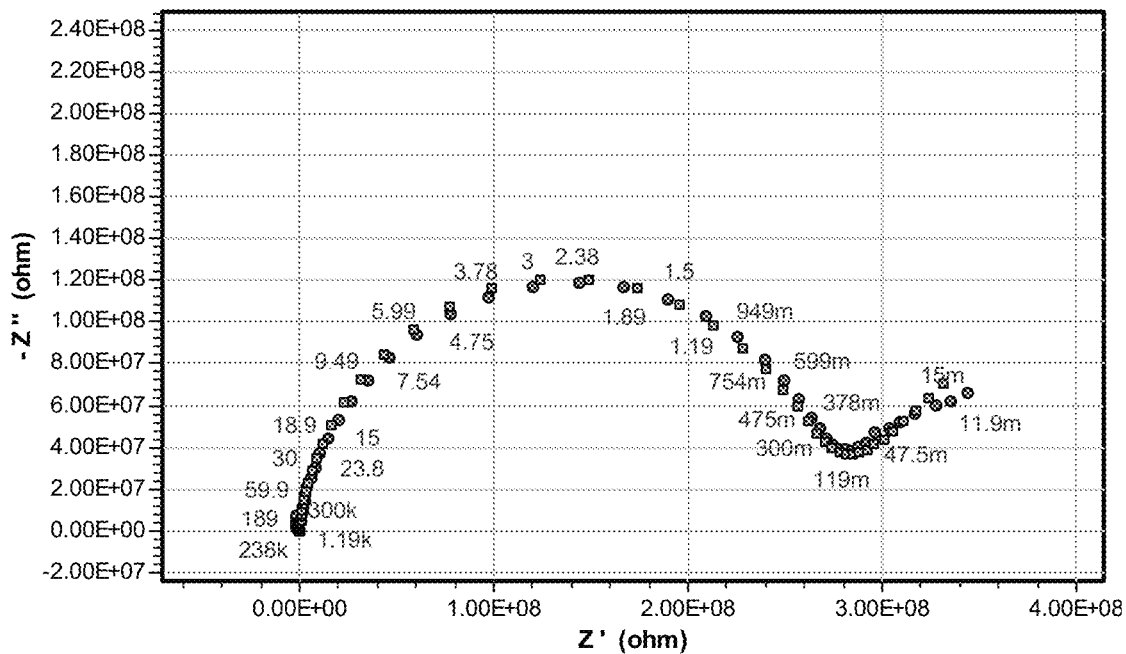
FIG. 5 shows a Nyquist plot of an impedance frequency response spectrum of a properly functioning sensor, according to an embodiment of the present disclosure.

FIG. 5 shows the measured impedance frequency response spectrum of a properly functioning Test Sensor 2, which is slightly different than that of Test Sensor 1 and, can be best fit with CPE instead of $C_g$. In FIG. 5, the square data points are fitting points obtained using the simulation software to fit the equivalent circuit using CPE, to the measured impedance. The data fit calculated an equivalent $C_g = 2.07 \times 10^4$ μF (where $Q_o = 2.5 \times 10^{-10}$ $S \cdot s^n$ and n=0.93), $R_g = 265$ MΩ and $W = 1.91 \times 10^7$ $\Omega \cdot s^{-1/2}$. These values are in line with expected capacitance, resistance and diffusion resistance of a properly functioning pH sensor. Thus, FIGS. 3 and 5 demonstrate how the method 100 can be used to characterize the performance of sensors.

Referring to FIG. 1, the components that can directly affect sensor performance include the membrane 16, working and reference electrodes 20, 22, the middle and front junctions 36, 38, the first, second and third electrolytes 30, 32, 34, and the front, middle and back seal 40, 42, 44 contacting the electrolytes. Any defect with the materials, solutions or structural integrity of these components may cause a sensor, namely a pH sensor, malfunction. Some of the commonly encountered failure modes in pH sensors include cracking, including micro-cracking, of membrane 16, electrolyte contamination, short circuit between electrodes, and poor insulation. Applicant discovered that certain characteristics of a measured impedance frequency response spectrum can be used to analyze and identify different failure modes in sensors. Accordingly, the method 100 was applied to pH sensors of different types having different defects embodied therein in several experiments described herein.

Experiment 1

Two sensor types (A: single junction pH sensor with liquid reference electrolyte; B: double junction pH sensor with wetted solid reference electrolyte) and totally six sensors were analyzed using the method 100. An initial pH test was conducted on each sensor in three buffer solutions, pH 4, 7 and 10 using the CM42 pH meter. The voltage output results (in mV) are contained in Table 1. The test data indicate that each of the sensors was not working properly except B-3, which was within specification in all three buffer solutions.

TABLE 1

Initial pH Test Data

| Sensor | mV reading in pH buffers | | | impedance (MΩ) in buffer 4 | mV reading pH - Ref (ext.) in buffer 4 | mV reading Ref - Ref (ext.) in buffer 4 |
|---|---|---|---|---|---|---|
| | 4<br>177.5 ± 12 | 7<br>0 ± 12 | 10<br>−177.5 ± 12 | | | |
| A-1 | no reading | | | 0 | 64 | no reading |
| A-2 | no reading | | | 0 | 163 | no reading |
| A-3 | 124 | −45 | −216 | 525 | 176 | 45 |
| B-1 | 107 | 11 | −85 | 583 | 179 | no reading |
| B-2 | 128 | 24 | −124 | 444 | 175 | no reading |
| B-3 | 168 | −6 | −180 | 759 | 180 | no reading |

Sensors A-1 and A-2 both showed zero membrane impedance, no pH (in mV) reading in all pH buffers. Note: a feature of the CM42 pH meter is to display no pH or mV reading when membrane impedance is too low. Sensors A-1 and A-2 further exhibited no reading from the reference electrode against an external reference electrode (i.e., Ref (ext.)). These results suggest that the sensors might have cracked pH glass bulbs, short circuits, or current leakage between the reference chamber and internal pH electrolyte through a cracked pH glass stem. The working to reference electrode output voltage (i.e., pH-Ref(ext)) reading of Sensor A-2 is slightly lower than specification, indicating the membrane is functioning but with some problem. The working to reference electrode output voltage reading of Sensor A-1 is much lower than specification but not zero. Such a result does not provide a clear clue about the failure. Conventionally, physical dissection and destruction of the sensor would be the only way to identify the root cause of the failure.

Figure 6A:
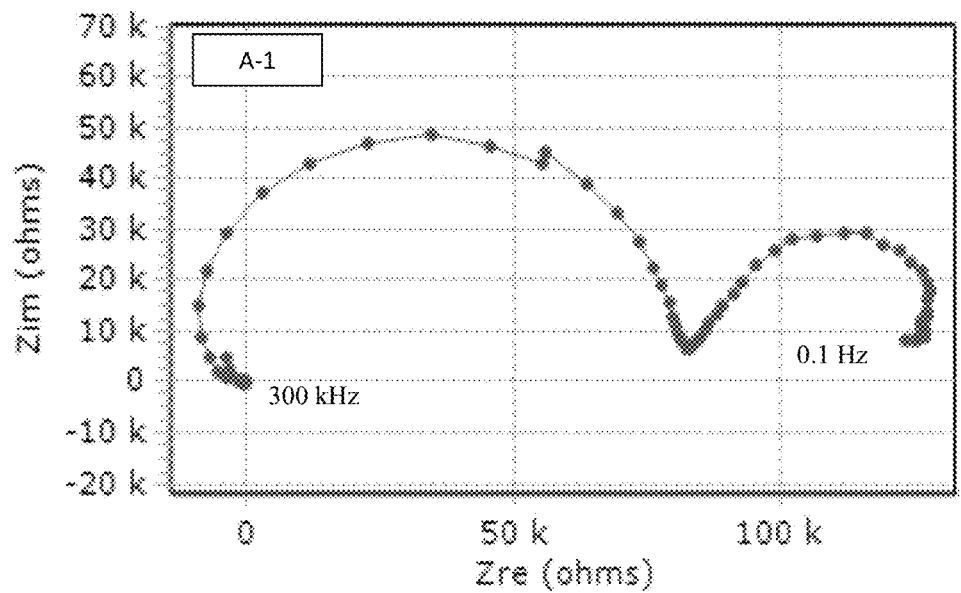
FIGS. 6A-6C show Nyquist plots of impedance frequency response spectra of exemplary defective sensors, according to an embodiment of the present disclosure.
Figure 6B:
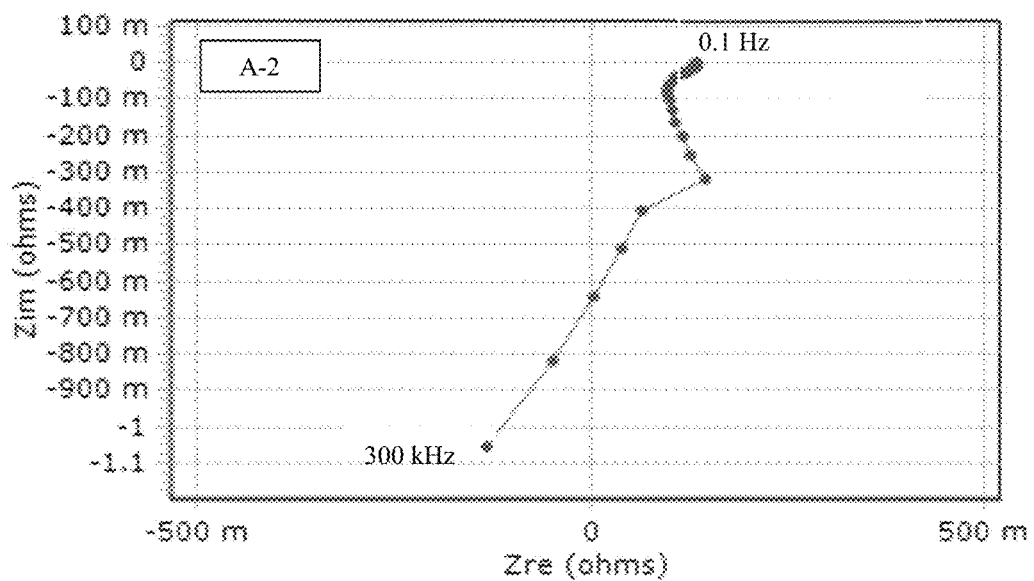
Figure 6C:
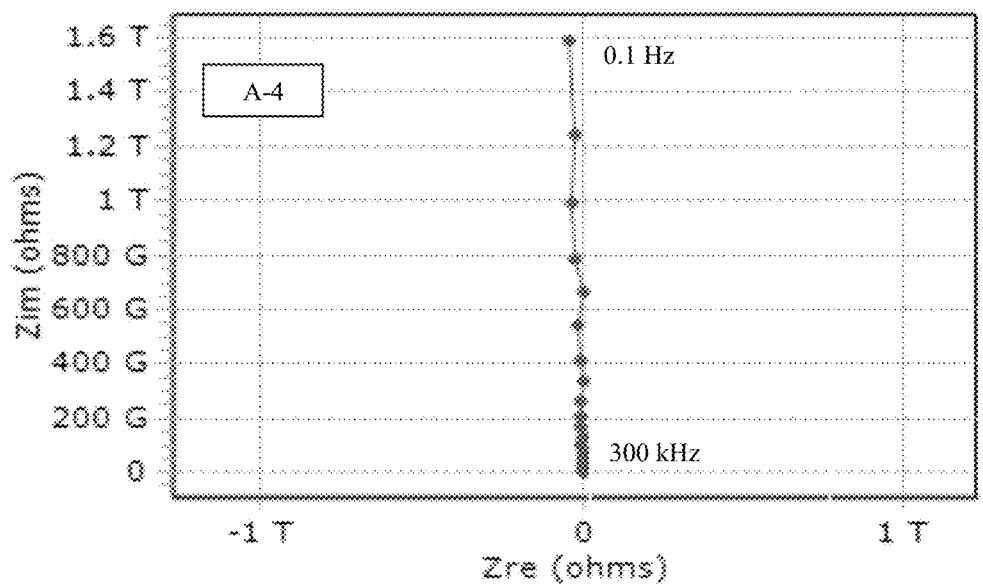

Applying the method 100, the measured impedance frequency response spectra of Sensors A-1 and A-2 clearly exhibit very different characteristics, as shown in FIGS. 6A and 6B. FIG. 6A shows a Nyquist plot of the response of Sensor A-1, showing two deformed semicircles with a total impedance less than 1 MΩ. Applicant has found that such a measured impedance frequency response spectrum is typical of a cracked membrane, for example, cracked pH bulbs. FIG. 6B shows a Nyquist plot of the response of Sensor A-2, showing an inductive component (i.e., negative imaginary impedance) and about zero total impedance. Applicant has found that such a measured impedance frequency response is typical of a short circuit, such as at the back seal or cable. A Sensor A-4 (not included in Table 1) containing an open circuit was evaluated using the method 100. FIG. 6C shows a Nyquist plot of the response of Sensor A-4, showing a nearly vertical line indicating extremely large (e.g., greater than 1 GΩ) total impedance with a positive imaginary part but nearly zero real part. Applicant has found that such a measured impedance frequency response is typical of an open circuit. These reported failure modes and correlated impedance frequency response characteristics have been corroborated and proven by physical dissection of Sensors A-1 and A-2 and many other test sensors.

The data in Table 1 indicate that Sensors A-3, B-1 and B-2 had glass impedance in normal range and a good pH-Ref (ext) reading, which suggest that the cause of failure is very likely due to the malfunction of their reference cells. Failure of the internal reference cell in these sensors was further confirmed with a measurement of their impedance frequency responses between the internal reference electrode (Ref) and an external reference electrode (Ref(ext)).

Figure 7:
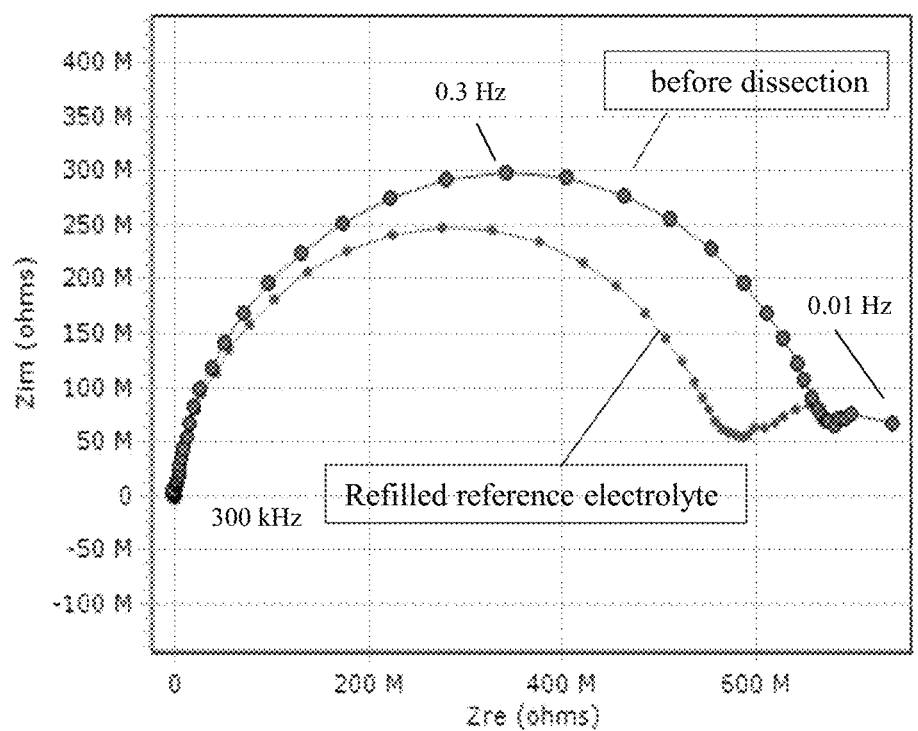
FIG. 7 shows Nyquist plots of impedance frequency response spectra of a defect sensor before and after a repair procedure, according to an embodiment of the present disclosure.

Among the key components of pH sensor reference cells, the reference electrolyte (i.e., the second electrolyte 32 for a single junction pH sensor; or the third electrolyte 34 for a double junction pH sensor) is commonly a point of failure. To investigate the failure mode of Sensor A-3 further, its reference electrolyte was replaced by drilling a hole through the housing of Sensor A-3, flushing out the reference electrolyte with deionized water, and refilling the emptied volume with fresh reference electrolyte. Then, the Sensor A-3 was tested and exhibited normal performance. FIG. 7 shows the measured impedance frequency response spectra before and after the replacement of the reference electrolyte. Thus, the differences of measured impedance frequency response characteristics have been proven useful for identifying reference cell failure modes as well.

Figure 8:
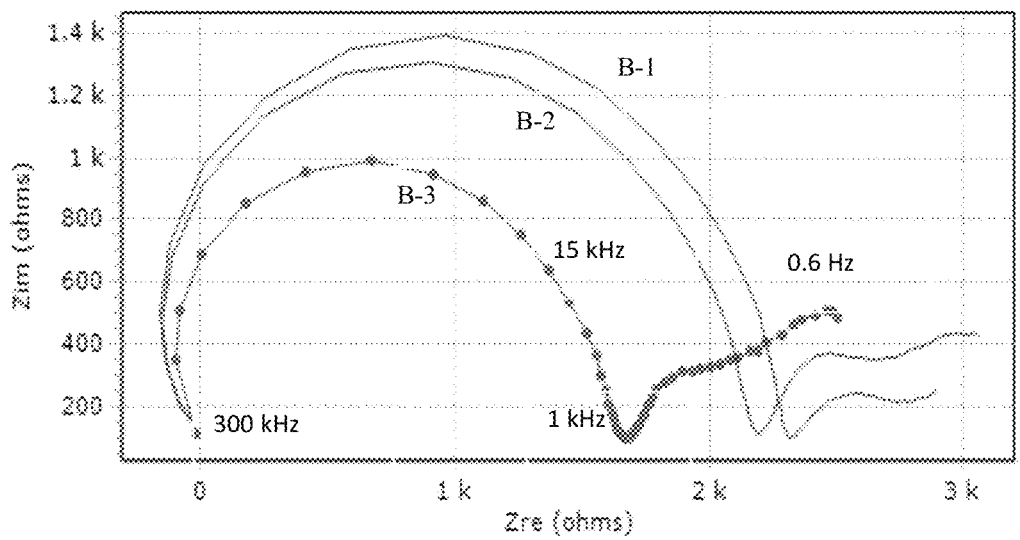
FIG. 8 shows Nyquist plots of impedance frequency response spectra of three test sensors, according to an embodiment of the present disclosure.

For Sensors B-1 and B-2, since the reference electrolyte was solid, refilling the reference electrolyte was not possible. Therefore, further information was sought concerning the reference electrolyte using the method 100. FIG. 8 shows the measured impedance frequency response spectra for the Sensors B-1, B-2 and B-3 measured between the reference electrode 22 and an external reference electrode (i.e., Ref-Ref(ext)). The three resulting impedance spectra shown in FIG. 8 generally have a similar shape, but the failed sensors (B-1 and B-2) have higher Ref-Ref(ext) impedance than the good sensor (B-3), indicating possibly lower porosity, smaller pore size, clogging of the pores, or simply higher material density of the failed sensors' reference electrolyte, where no other defects are found with the reference cells. Thus, FIG. 8 demonstrates that the method 100 may provide valuable guidance for further analysis and problem solving of such failure modes.

Experiment 2

The method 100 was further applied to characterize and analyze the effects of steam sterilization on the glass membrane in a pH sensor, such as the sensor 10. Steam sterilizable ("SS") pH sensors having membranes made with old SS glass and new SS glass were tested and compared with two SS pH sensors made by other manufactures (i.e., Sensors C1 and C2). The terms old SS glass and new SS glass simply indicate two different types of glass membranes used in the sensors under test. One means of simulating the effects of the steam sterilization process on a pH sensor is to condition the sensor in a steam-in-place ("SIP") test. The SIP test used in each experiment disclosed herein included inserting at least the membrane of the pH sensor in a pipe conveying steam of at least 100° C. for 30 minutes, cooling the sensor down to room temperature, then repeating the steam exposure and cooling processes for a total of three cycles. After the SIP test, the sensors were soaked in a 3 molar potassium chloride (KCl) solution for 60 hours.

Table 2 contains the pH test results and measured impedance frequency response data using the method 100 for the pH sensor with old SS glass before and after the SIP test and after surface treatment. The surface treatment included etching and cleaning the glass membrane with hydrofluoric acid (i.e., HF). "Etching I" indicates that the outside surface of the glass membrane was treated for 5 minutes (mins) in 10% HF and cleaned with deionized water. "Etching II" indicates that the inside surface of the glass membrane was treated for 5 minutes (mins) in 10% HF and cleaned with deionized water. The old SS glass sensor was evaluated using method 100 between each conditioning and treatment step. The impedance spectra data (C, R, $Y_o$, and $\sigma$) in Table 2 were calculated using the simulation software with the equivalent circuit shown in FIG. 4B.

TABLE 2 pH Test and Impedance Data of a Sensor Made with Old SS Glass

| Condition | mV reading in pH buffers | | | response time (s) | C (pF) | R (MΩ) | $Y_o$ (S · $s^{1/2}$) | $\sigma$ (MΩ $s^{-1/2}$) |
| --- | --- | --- | --- | --- | --- | --- | --- | --- |
| | 4<br>177.5 ± 12 | 7<br>0 ± 12 | 10<br>−177.5 ± 12 | | | | | |
| new | 170 | −5 | −177 | 15 | 370 | 460 | 5.80 × $10^{-8}$ | 12 |
| after SIP | 162 | −26 | −199 | 50 | 371 | 400 | 7.83 × $10^{-9}$ | 90 |
| after etching I | 172 | 5 | −175 | 34 | 465 | 327 | 1.8 × $10^{-8}$ | 39 |

After the SIP test, the sensor was out of specification. Specifically, though the capacitance and resistance of the glass membrane were comparable to that of the sensor before SIP exposure, the Warburg coefficient ($\sigma$) representing diffusion resistance, increased from 12 to 90 MΩ·$s^{-1/2}$. After etching I, the voltage output of sensor in the three standard pH buffer solutions was back to normal, although response time was still longer than a new sensor. Without being bound to a specific theory, Applicant suggests that the etching surface treatment caused the glass membrane to become thinner and hence lower in resistance and higher in capacitance, while at the same time the diffusion resistance (i.e., the Warburg coefficient) also decreased to 39 MΩ·$s^{-1/2}$.

Figure 9A:
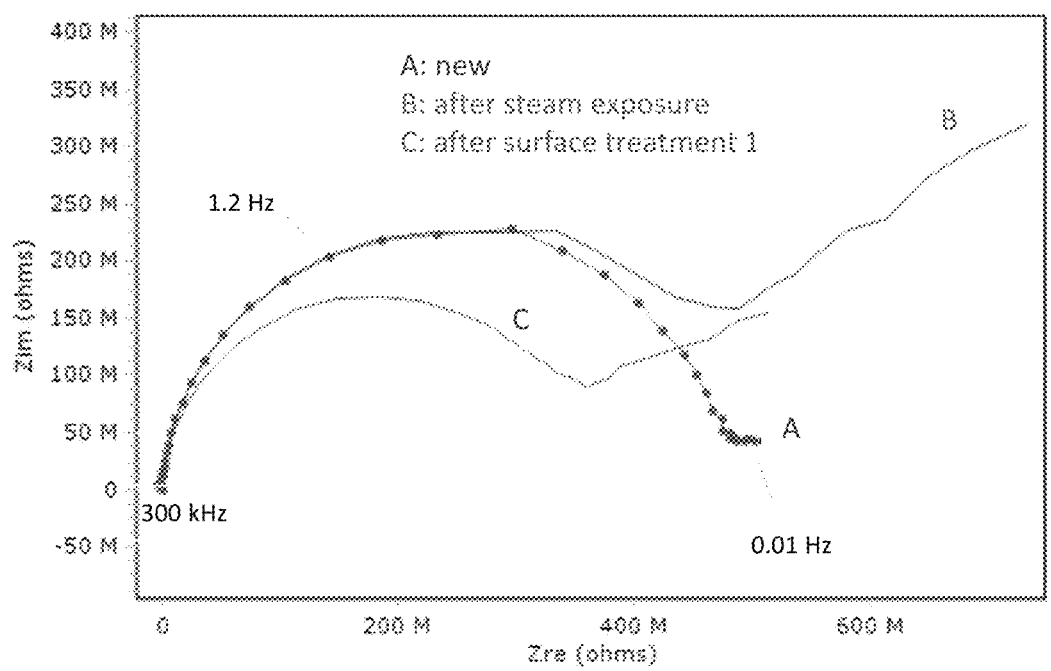
FIGS. 9A and 9B show Nyquist plots of impedance frequency response spectra of a test sensor before and after conditioning and surface treatment, according to an embodiment of the present disclosure.
Figure 9B:
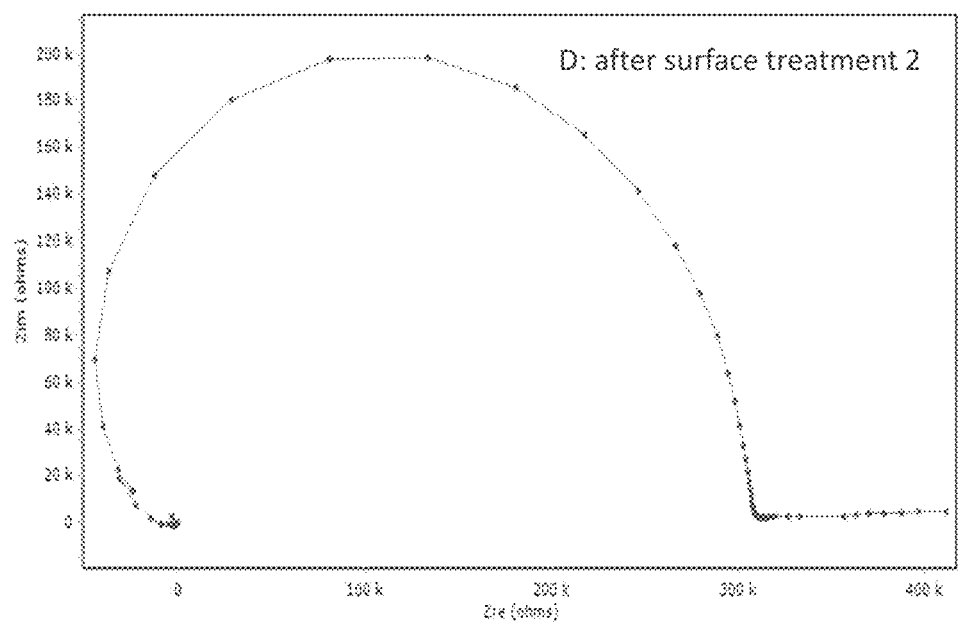

FIG. 9A shows the impedance spectra of the old SS glass sensor before and after SIP test and after etching I of the pH glass membrane. FIG. 9B shows the impedance spectra of the old SS glass sensor after etching II of the pH glass membrane. As shown in FIG. 9B, after etching II, the sensor functioned similar to new. Applicant suggests that the etching II treatment caused the glass membrane to become even thinner and thus further lowered impedances. After the second surface treatment, the shape of the impedance spectrum was generally similar to that of a new sensor. Consequently, the method 100 indicates and quantifies how the SIP process changed the material of the glass membrane and how the material change very likely occurred only in a limited layer on the outside and inside surfaces of the glass membrane.

Experiment 3

The method 100 was further applied to characterize and analyze the effects of steam sterilization on the glass membrane in pH sensors, such as the sensor 10, manufactured by other manufacturers. Steam sterilizable ("SS") pH sensors having membranes made with new SS glass manufactured by the Applicant (labeled "E+H") were tested and compared with two SS pH sensors made by other manufactures (i.e., Sensors C1 and C2). The SIP test described with respect to Experiment 2 was used to condition the sensor test samples in Experiment 3 as well.

Table 3 contains the pH test results and measured impedance frequency response data using the method 100 for Applicant's pH sensor (i.e., Sensor E+H) and for Sensors C1 and C2 before the SIP test. The impedance spectra data (C, R, $Y_o$, and $\sigma$) in Table 3 were calculated using the simulation software with the equivalent circuit shown in FIG. 9B. The $\sigma$ values were calculated using EQN. 5, and the C values were calculated with using EQN. 7. The highlighted mV datum is out of specification.

TABLE 3 pH Test and EIS Data of SS pH Sensors as New

| pH Sensor | mV reading in pH buffers | | | C (pF) | R (MΩ) | $Y_o$ (S · $s^{1/2}$) | $\sigma$ (Ω $s^{-1/2}$) | $|Z|_{total}$ at 0.01 Hz (MΩ) |
| --- | --- | --- | --- | --- | --- | --- | --- | --- |
| | 4<br>177.5 ± 12 | 7<br>0 ± 12 | 10<br>−177.5 ± 12 | | | | | |
| C1 | 174 | 0 | −170 | 79 | 190 | 2.10 × $10^{-8}$ | 34 | 336 |
| C2 | 179 | 5 | −164 | 317 | 434 | 7.52 × $10^{-8}$ | 9 | 462 |
| E + H | 172 | −3 | −174 | 207 | 265 | 3.70 × $10^{-8}$ | 19 | 341 |

Table 4 contains the pH test results and measured impedance frequency response data using the method 100 for Applicant's pH sensor (i.e., Sensor E+H) and for Sensors C1 and C2 after the SIP test. The impedance spectra data (C, R, $Y_o$, and $\sigma$) in Table 4 were calculated using the simulation software with the equivalent circuit shown in FIG. 9B. The $\sigma$ values were calculated using EQN. 5, and the C values were calculated with using EQN. 7. The highlighted mV data are out of specification.

TABLE 4 pH Test and EIS Data of the SS pH Sensors after SIP Test

| pH Sensor | mV reading in pH buffers | | | C (pF) | R (MΩ) | $Y_o$ (S·s$^{1/2}$) | σ (Ω s$^{-1/2}$) | $|Z|_{total}$ at 0.01 Hz (MΩ) |
|---|---|---|---|---|---|---|---|---|
| | 4<br>177.5 ± 12 | 7<br>0 ± 12 | 10<br>-177.5 ± 12 | | | | | |
| C1 | 149 | 22 | -193 | 66 | 160 | 1.14 × 10$^{-8}$ | 62 | 472 |
| C2 | 164 | 9 | -177 | 294 | 356 | 1.59 × 10$^{-8}$ | 45 | 547 |
| E + H | 170 | 2 | -177 | 200 | 280 | 7.20 × 10$^{-9}$ | 98 | 723 |

Figure 10A:
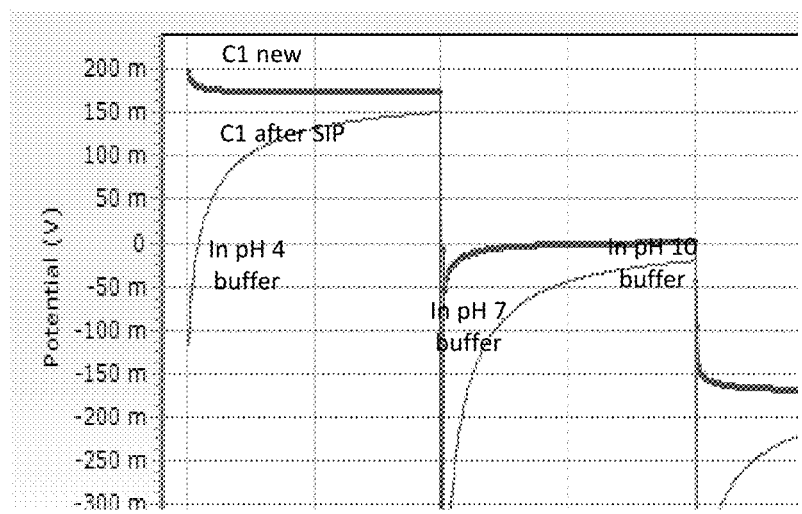
FIGS. 10A-10C show pH measurements in millivolts (mV) against time in seconds (s) for test sensors before and after conditioning, according to an embodiment of the present disclosure.
Figure 10B:
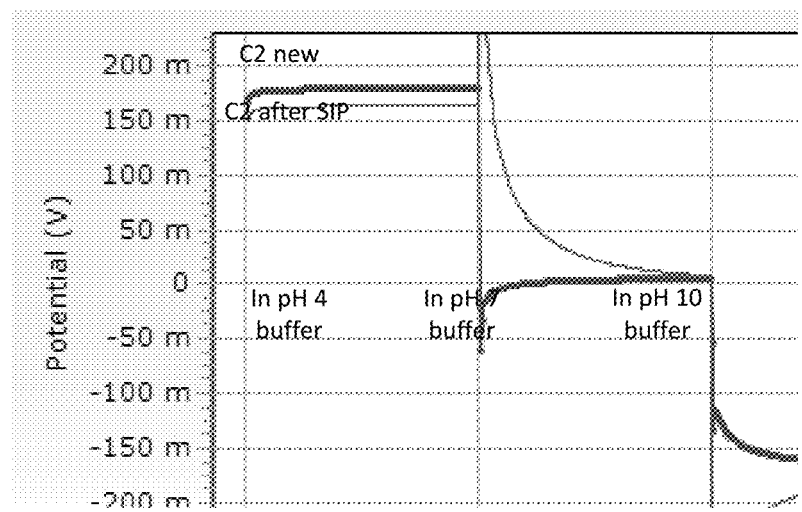
Figure 10C:
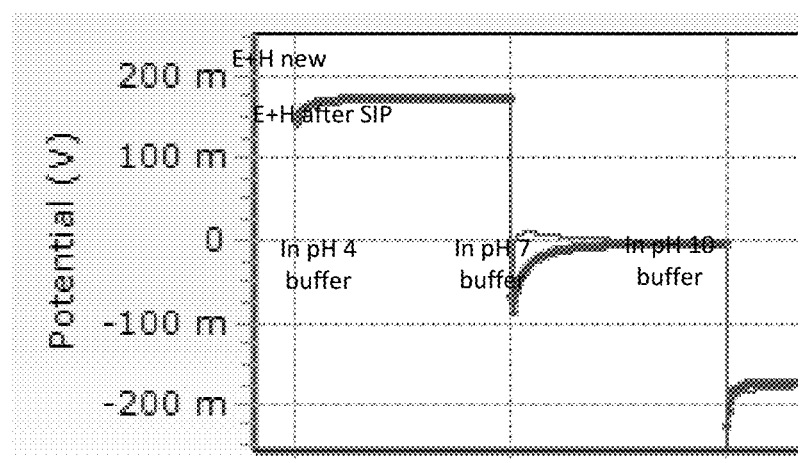
Figure 11A:
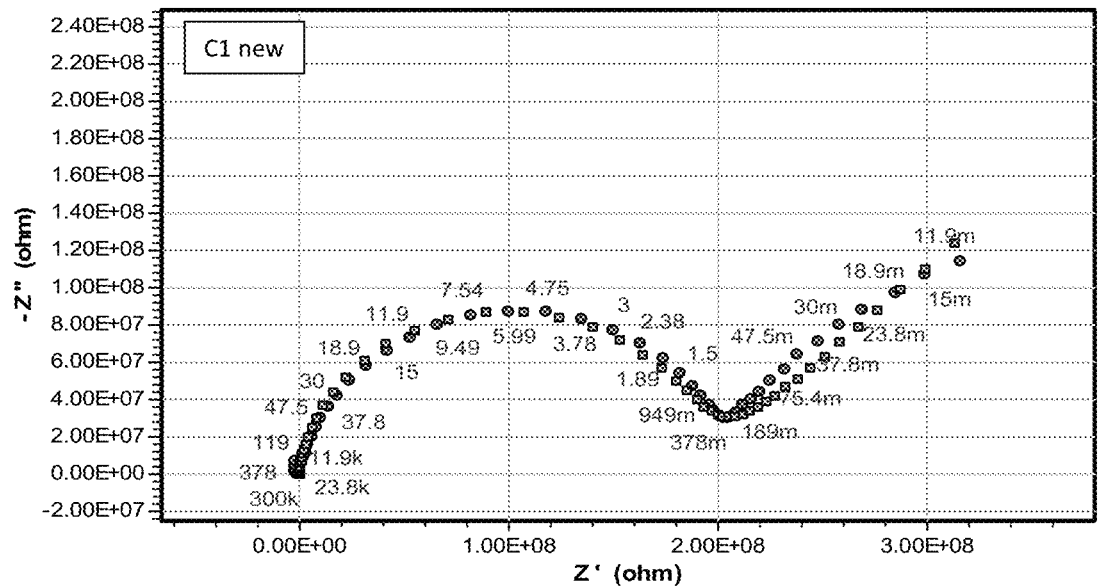
FIGS. 11A-11F show Nyquist plots of impedance frequency response spectra of three test sensors before and after conditioning, according to an embodiment of the present disclosure.
Figure 11B:
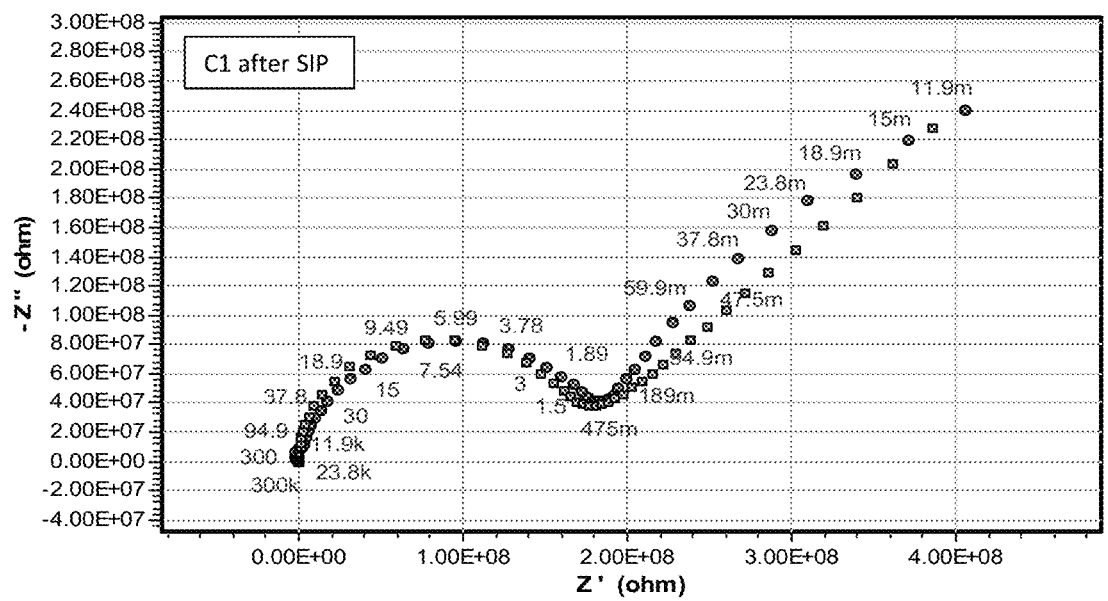
Figure 11C:
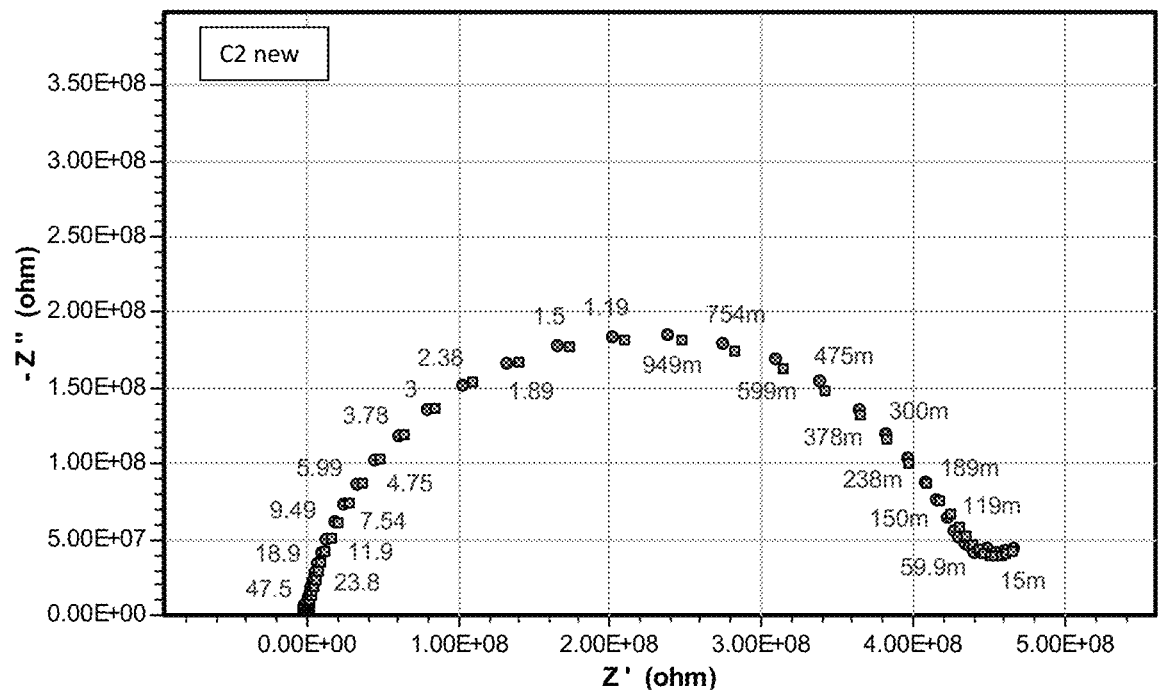
Figure 11D:
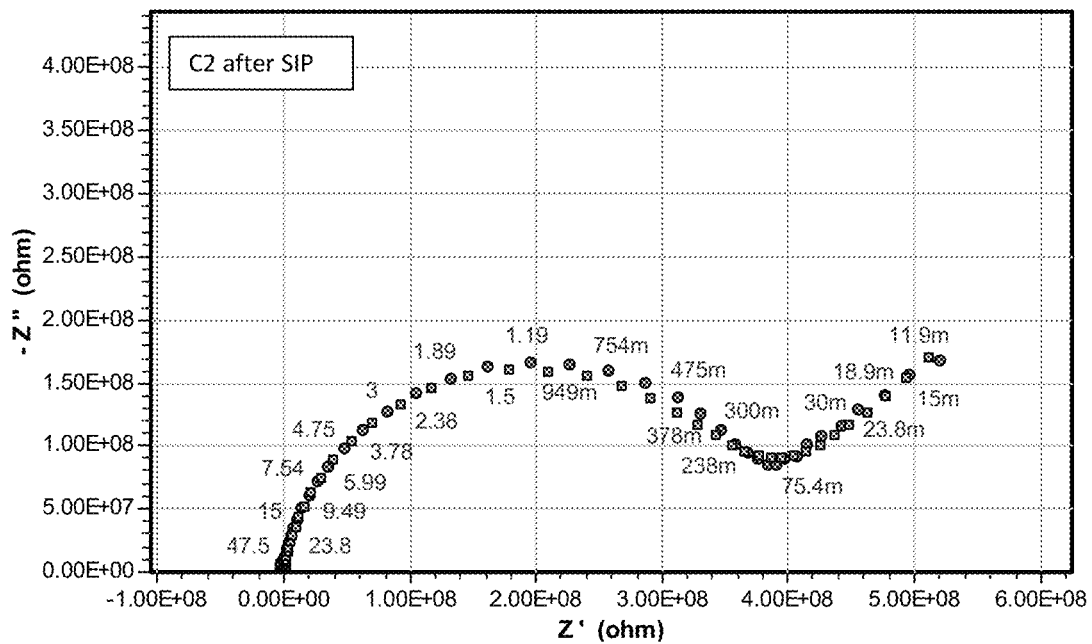
Figure 11E:
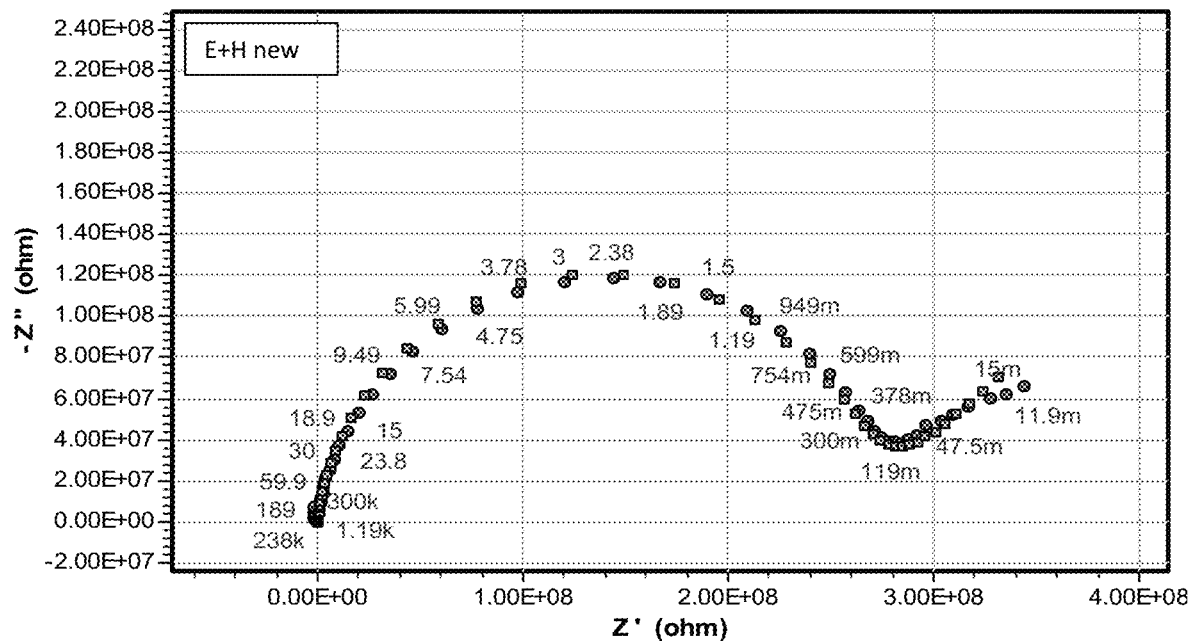
Figure 11F:
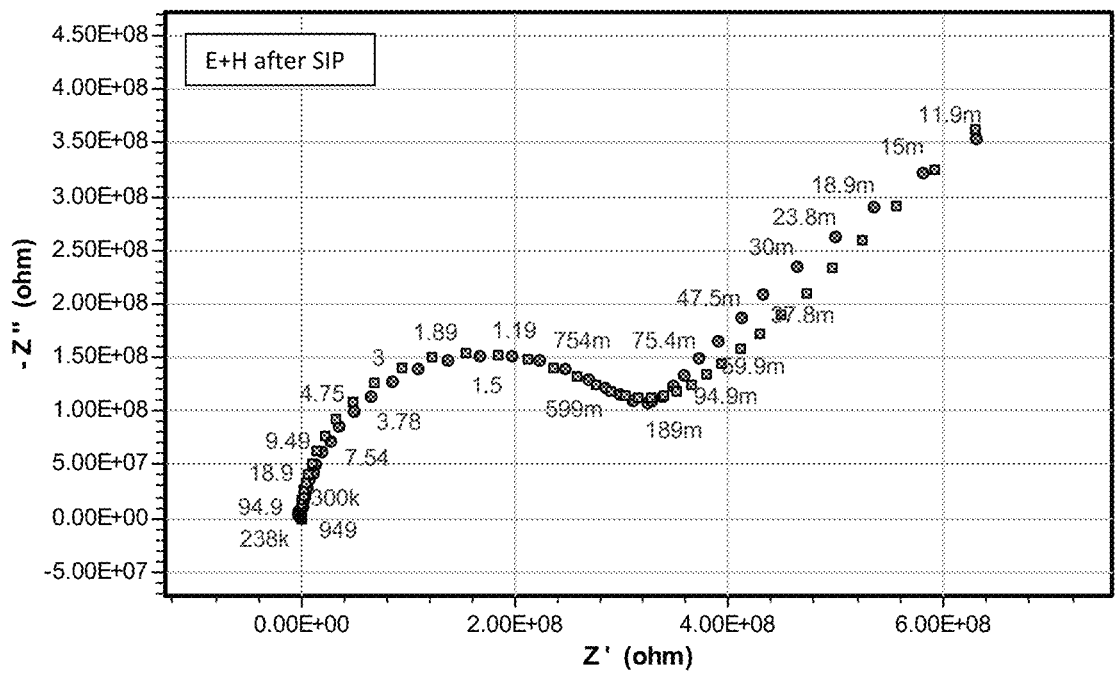

FIGS. 10A-10C show the time-based pH test results in voltage output (i.e., mV readings versus time) of the E+H, C1 and C2 sensors before and after the SIP test. FIGS. 11A-11F show the Nyquist plots of the measured impedance frequency response spectra for the three sensors before and after SIP test. The circular dots are measured data points; the squares are fitted data points.

The pH test results of Tables 3 and 4 indicate: (1) the three SS pH sensors were all within specifications before SIP test, except that Sensor C2 was slightly lower than specification in pH 10 buffer; and (2) after the SIP test, Sensor C1 was completely out of specification, Sensor C2 was within specification in pH 7 and 10 buffers but slightly below specification in pH 4 buffer, and Sensor E+H was within specification in all three pH buffers. From FIGS. 10A-10C, Sensor E+H had a faster response than either Sensor C1 or C2.

The measured impedance frequency response spectra of FIGS. 11A-11F show: (1) the three sensors have no significant difference on total glass impedance (either before or after SIP test), which is in the normal range of pH sensors; (2) Sensor E+H exhibited lower resistance and capacitance than Sensor C2, which at least partially explains Sensor E+H's faster response because lower resistance and capacitance yields a smaller RC time constant and hence faster charge and discharge processes; and (3) if the capacitance is too low, the glass membrane does not have enough sensing capability for the H$^+$ in a test solution, as in the case of Sensor C1 after the SIP test (capacitance, C, was only 66 pF). Further, the point of balance between response time and sensing capability seems to be somewhere between 66 pF and 79 pF for Sensor C1.

As demonstrated by the Experiments 1, 2 and 3, the method 100 provides an understanding the effects of a sensor's impedance components, both individually and interactively, on sensor performance, and the method 100 enables a correlation between sensor impedance components and sensor performance. Moreover, the method 100 was shown to be very useful for failure mode analysis of sensors, particularly for identifying glass bulb cracks, short circuits, open circuit, and reference cell problems in pH sensors. Further, the method 100 was shown to be useful for evaluating the effects of material type, operating conditions and surface treatments on sensor performance. Therefore, the method 100 may be applied to both quality control of manufactured sensors and root cause failure mode analysis of sensors deployed in the field.

Accordingly, in at least one embodiment, the step 110 of the method 100 may include identifying whether the total impedance is below a lower threshold or above an upper threshold and/or whether the imaginary component of the total impedance is predominantly greater than or less than zero. Using the method 100, a sensor in which the total impedance is below the lower threshold and the imaginary component is predominantly greater than zero may be characterized as having a defect in a membrane of the sensor. A sensor in which the total impedance is below the lower threshold and the imaginary component is predominantly less than zero may be characterized as having a short circuit. Further, a sensor in which the total impedance at the law frequency end is above the upper threshold and the real/imaginary component ratios are predominantly less than a ratio threshold is characterized as having an open circuit. In certain embodiments, determining whether the real/imaginary component ratio is predominantly less than the ratio threshold may include.

In certain embodiments of the method 100, the lower threshold may be around 5 megaohms, and the upper threshold may be about 50 megaohms. In alternative embodiments, the lower threshold may be around 10 megaohms, and the upper threshold may be about 5 gigaohms. In at least one embodiment, the lower threshold may be around 1 In certain embodiments of the method 100, the ratio threshold may be around 0.1. In certain embodiments, additionally or alternatively, the upper, lower and ratio thresholds may be ranges. The upper, lower and ratio threshold values disclosed are merely exemplary values. In operation, specific upper, lower and ratio threshold ranges and values to be applied in the method 100 for a given type of sensor are determined for the specific sensor type by characterizing a properly functioning sensor. Consequently, the appropriate upper, lower and ratio threshold values and/or ranges for a given implementation of the method 100 may be different than the exemplary values disclosed herein.

While various embodiments of a method for characterizing and analyzing a sensor have been described in considerable detail herein, the embodiments are merely offered by way of non-limiting examples of the disclosure described herein. It will therefore be understood that various changes and modifications may be made, and equivalents may be substituted for elements and steps thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Such sequences may be varied and still remain within the scope of the present disclosure. Therefore, the particular order of the steps disclosed herein should not be construed as limitations of the present disclosure.

The invention claimed is:

1. A method of characterization and failure analysis of a measuring sensor, the method comprising:

applying an alternating current having a frequency at a selected voltage to a sensor, wherein the voltage is applied between a reference electrode and a working electrode of the sensor, and wherein the sensor is an electrochemical sensor having a membrane;

varying the frequency of the alternating current between a lower frequency and an upper frequency over a range having a low frequency end and an upper frequency end, wherein the varying defines a scan;

measuring an impedance of the sensor between the reference electrode and the working electrode from a single scan over the range of frequencies of the alternating current;

analyzing the measured impedance to determine a total impedance of the sensor and the real and imaginary components of the total impedance at and over the applied frequencies of the alternating current; and determining whether, based on the total impedance and on the real and imaginary components of the total impedance of the sensor, the sensor has a crack in the membrane of the sensor or a short circuit or an open circuit between electrodes of the sensor.

2. The method of claim 1, the method further comprising generating a measured impedance frequency response spectrum.

3. The method of claim 1, wherein the determining includes identifying whether the total impedance at the low frequency end is below a lower threshold or above an upper threshold and/or whether imaginary components at various frequencies are predominantly greater than or less than zero.

4. The method of claim 3, wherein a sensor in which the total impedance at low frequency end is below the lower threshold and the imaginary components at various frequencies are predominantly greater than zero is determined to have a crack in a membrane of the sensor.

5. The method of claim 3, wherein a sensor in which the total impedance at low frequency end is below the lower threshold and the imaginary components at various frequencies are predominantly less than zero is determined to have a short circuit.

6. The method of claim 3, wherein the lower threshold is around 5 megaohms, and the upper threshold is about 50 megaohms.

7. The method of claim 3, wherein the lower threshold is around 10 megaohms, and the upper threshold is about 5 gigaohms.

8. The method of claim 3, wherein a sensor in which the total impedance at a low frequency end is above the upper threshold and the real/imaginary component ratio at various frequencies are predominantly less than a threshold is determined to have an open circuit.

9. The method of claim 8, wherein the upper threshold is about 5 gigaohms and the ratio threshold is around 0.1.

10. The method of claim 1, the method further comprising:
data fitting the measured impedance to generate a simulated response spectrum; and
applying an equivalent circuit model to the simulated response spectrum to estimate the capacitance, resistance and Warburg coefficient of the sensor.

11. The method of claim 10, the method further comprising predicting a performance of the sensor using the estimated the capacitance, resistance and Warburg coefficient.

12. The method of claim 1, wherein the analyzing includes generating a plot of the measured impedance as a function of the frequency of the alternating current to yield a frequency response spectrum.

13. The method of claim 12, wherein the plot is a Nyquist plot.

14. The method of claim 1, wherein the frequency of the alternating current is varied over a spectrum.

15. The method of claim 1, wherein the frequency of the alternating current is varied between discrete predetermined frequencies.

16. The method of claim 1, wherein the sensor is a pH sensor.

17. The method of claim 1, wherein the reference electrode is an external reference electrode connected to or associated with the sensor.

18. The method of claim 1, wherein the determining is a step in a quality control process.

19. The method of claim 1, wherein the determining includes determining a failure mode of the sensor.

20. The method of claim 1, wherein the determining includes checking a status of the sensor.

21. The method of claim 1, wherein the sensor includes equipment suitable to perform the measuring of the impedance of the sensor at various frequencies.

22. The method of claim 21, wherein the equipment is integrated into a plug head of the sensor.

* * * * *